United States Patent
Ditrich et al.

(10) Patent No.: US 8,008,062 B2
(45) Date of Patent: Aug. 30, 2011

(54) PRODUCTION OF (R)- AND (S)-4-(1-AMINOETHYL) BENZOIC ACID METHYL ESTER SULFATE BY LIPASE ACYLATION OF RACEMIC 4-(1-AMINOETHYL) BENZOIC ACID METHYL ESTER AND SULFURIC ACID PRECIPITATION

(75) Inventors: Klaus Ditrich, Gönnheim (DE); Harald Winsel, Birkenheide (DE); Dominique Moulin, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 665 days.

(21) Appl. No.: 12/159,283

(22) PCT Filed: Dec. 19, 2006

(86) PCT No.: PCT/EP2006/069890
§ 371 (c)(1),
(2), (4) Date: Jun. 26, 2008

(87) PCT Pub. No.: WO2007/077120
PCT Pub. Date: Jul. 12, 2007

(65) Prior Publication Data
US 2008/0305530 A1    Dec. 11, 2008

(30) Foreign Application Priority Data

Dec. 28, 2005  (DE) .................. 10 2005 062 966
Jan. 6, 2006   (DE) .................. 10 2006 001 160

(51) Int. Cl.
*C12P 41/00* (2006.01)
*C07C 211/03* (2006.01)

(52) U.S. Cl. ........................ 435/280; 564/282

(58) Field of Classification Search .................. None
See application file for complete search history.

(56) References Cited

U.S. PATENT DOCUMENTS 5,728,876 A    3/1998   Balkenhohl et al.

FOREIGN PATENT DOCUMENTS

| EP | 1029851 A1 | 8/2000 |
| WO | WO-91/19002 A1 | 12/1991 |
| WO | WO-95/08636 A1 | 3/1995 |
| WO | WO-2005/105732 A1 | 11/2005 |

OTHER PUBLICATIONS

Dickins, R.S., et al., "Synthesis, Time-Resolved Luminescence, NMR Spectroscopy, Circular Dichroism and Circularly Polarised Luminescence Studies of Enantiopure Macrocyclic Lanthanide Tetraamide Complexes", Chem. Eur. J., 1999, vol. 5, No. 3, pp. 1095-1105.
Kitagucki, H., et al, "Enzymatic Resolution of Racemic Amines: Crucial Role of the Solvent", J. Amer. Chem. Soc., 1989, vol. 111, pp. 3094-3095.
Gotor, V., et al, "Enantioselective Acylation of Amino Alcohols by Porcine Pancreatic Lipase", J. Chem. Soc. Chem. Commun., 1988, pp. 957-958.
Brieva, R., et al, "Enzymatic Synthesis of Amides with Two Chiral Centres", J. Chem. Soc. Chem. Commun., 1990, pp. 1386-1387.

*Primary Examiner* — Sandy Saucier
(74) *Attorney, Agent, or Firm* — Connolly Bove Lodge & Hutz LLP

(57) ABSTRACT

A method for preparing optically active methyl 4-(1-ammoniumethyl)benzoate sulfate by reacting racemic methyl 4-(1-aminoethyl)benzoate with an acylating agent in the presence of a lipase to give methyl 4-(1-aminoethyl)benzoate and subsequently precipitating methyl 4-(1-ammoniumethyl)benzoate sulfate by adding sulfuric acid.

7 Claims, No Drawings

PRODUCTION OF (R)- AND (S)-4-(1-AMINOETHYL) BENZOIC ACID METHYL ESTER SULFATE BY LIPASE ACYLATION OF RACEMIC 4-(1-AMINOETHYL) BENZOIC ACID METHYL ESTER AND SULFURIC ACID PRECIPITATION

RELATED APPLICATIONS

This application is a national stage application (under 35 U.S.C. §371) of PCT/EP2006/069890, filed Dec. 19, 2006, which claims benefit of German application 10 2005 062 966.0, filed Dec. 28, 2005 and German application 10 2006 001 160.0, filed Jan. 6, 2006.

The present invention relates to a novel method for method for preparing methyl (R)—and (S)-4-(1-ammoniumethyl) benzoate sulfate.

PRIOR ART

The resolution of racemates of amines by enzyme-catalyzed reaction with esters is known. Kitaguchi et al. (J. Amer. Chem. Soc. 111, 3094-3095, 1989) describe the resolution of racemates of amines using trifluoroethyl butyrate with subtilisin catalysis. The enantioselectivity of this reaction is, however, very dependent on the solvent. Even with the most suitable of the solvents described (3-methyl-3-pentanol), only moderate selectivity is achieved.

WO 91/19002 describes a method for chiral enrichment of racemic primary amines in which the amines are reacted with ethyl acetate or ethyl butyrate with subtilisin catalysis. The enantiomeric excesses achieved thereby are, however, unsatisfactory; in addition, long reaction times of from one to several weeks are required.

Gotor et al. (J. Chem. Soc. Chem. Commun. 957-958, 1988) describe the enantioselective acylation of 2-aminobutan-1-ol with ethyl acetate with catalysis by porcine pancreatic lipase (PPL). In this case, the ester used (ethyl acetate) is also employed as solvent. No satisfactory results are achieved on use of other solvents or other enzymes.

Brieva et al. (J. Chem. Soc. Chem. Commun., 1386-1387, 1990) describe the enantioselective synthesis of amides from racemic primary amines by reaction with 2-chloropropionate with catalysis by subtilisin in hexane or *Candida cylindracea* lipase in 3-methyl-3-pentanol.

WO 95/08636 describes a method for preparing optically active primary and secondary amines from the corresponding racemates by enantioselective acylation in the presence of a hydrolase.

The optically active amines prepared in this way are, however, depending on their structure not very stable on storage and are subject to further side reactions.

The object therefore was to provide a method which ensured the preparation of optically active methyl 4-(1-aminoethyl)benzoate in high yield, optical purity and high stability on storage.

DESCRIPTION OF THE INVENTION

The invention relates to a method for preparing optically active methyl 4-(1-ammoniumethyl)benzoate sulfate by reacting racemic methyl 4-(1-aminoethyl)benzoate with an acylating agent in the presence of a lipase to give methyl 4-(1-aminoethyl)benzoate and subsequently precipitating methyl 4-(1-ammoniumethyl)benzoate sulfate by adding sulfuric acid.

The acylating agents suitable for the method of the invention are preferably carboxylic esters. So-called activated carboxylic esters in which the acid component has a heteroatomic substitution in the alpha-position to the carbonyl carbon atom are particularly preferred. Methoxyacetic esters are preferably employed as acylating agents. The alcohol component of the carboxylic ester preferably consists of alkyl alcohols having a chain length of 1-6 C atoms, which may be branched or unbranched and also substituted. Isopropyl methoxyacetate is a particularly suitable acylating agent.

A large number of enzymes can be employed as lipases in the method of the invention. Especially preferred are microbial lipases which can be isolated for example from yeasts or bacteria. Particularly suitable lipases are those from *Pseudomonas*, e.g. Amano P, or the lipases from *Pseudomonas* spec. DSM 8246 or *Candida antarctica*. The lipase marketed by Novozymes under the name Novozyme 435® (Lipase B from *Candida antarctica*) is particularly suitable for the method of the invention.

The enzyme used can be employed in native or in immobilized form.

Suitable solvents are in general organic solvents. The reaction proceeds particularly well in ethers, for example in MTBE or THF, or in hydrocarbons such as hexane, cyclohexane, toluene or halogenated hydrocarbons such as methylene chloride. The reaction can, however, also be carried out in the absence of a solvent.

Reaction of the acylating agent with the racemic methyl 4-(1-aminoethyl)benzoate with enzyme catalysis is normally carried out at room temperature. The reaction times therefor are from 1 to 48 hours, preferably 5-24 hours.

1 to 2 mol, preferably 1.2 to 1.6 mol, of acylating agent are added per mole of methyl 4-(1-aminoethyl)benzoate.

The amount of lipase to be added depends on the type of lipase and the activity of the enzyme preparation. The amount of lipase optimal for the reaction can easily be ascertained by simple preliminary tests. Ordinarily, 1000 units of lipase are added per mmol of amine.

The progress of the reaction can easily be followed by conventional methods, for example by gas chromatography. In the case of racemate resolution, it is sensible to stop the reaction when the conversion of the racemic amine is 50%. This takes place ordinarily by removing the catalyst from the reaction space, for example by filtering off the enzyme.

The enantioselective reaction of the racemic methyl 4-(1-aminoethyl)benzoate with the lipase results in the correspondingly acylated product (amide) from one enantiomer, while the other enantiomer remains unchanged. The mixture of amine and amide which is now present can easily be separated by conventional methods. Extraction or distillation methods are for example very suitable for separating the mixture of amine and amide. The enantiomer which is selectively acylated depends on the choice of the lipase and can easily be ascertained by a preliminary test; Novozyme® 435 for example selectively acylates the methyl (R)-4-(1-aminoethyl)benzoate.

After optically active methyl 4-(1-aminoethyl)benzoate has been prepared, it is converted by addition of sulfuric acid into optically active methyl 4-(1-ammoniumethyl)benzoate sulfate. At least 0.5 mol of sulfuric acid is added per mol of methyl 4-(1-aminoethyl)benzoate in the reaction in order to ensure complete salt formation (conversion into methyl 4-(1-ammoniumethyl)benzoate sulfate).

The sulfuric acid can be added directly on the enzymatic acylation or else after previous isolation of methyl 4-(1-aminoethyl)benzoate from the reaction medium. It is also possible only to remove the lipase from the reaction medium; this is particularly advantageously applied when immobilized lipase is used.

The methyl 4-(1-ammoniumethyl)benzoate sulfate ordinarily precipitates from the reaction medium and can thus easily be separated from the dissolved acylated methyl 4-(1-aminoethyl)benzoate (i.e. the amide). If both reaction products are in dissolved form, they can easily be separated on the basis of their different physicochemical properties by standard operations such as crystallization, extraction, distillation and chromatography.

Methyl 4-(1-ammoniumethyl)benzoate sulfate is stable under the reaction conditions and undergoes no intermolecular amidation as is observed for example with methyl 4-(1-aminoethyl)benzoate. Methyl 4-(1-ammoniumethyl)benzoate sulfate can be obtained in high optical purity by further purification such as recrystallization.

EXPERIMENTAL SECTION

Example 1

Preparation of Methyl (S)-4-(1-Ammoniumethyl) Benzoate Sulfate (S-1-Sulfate)

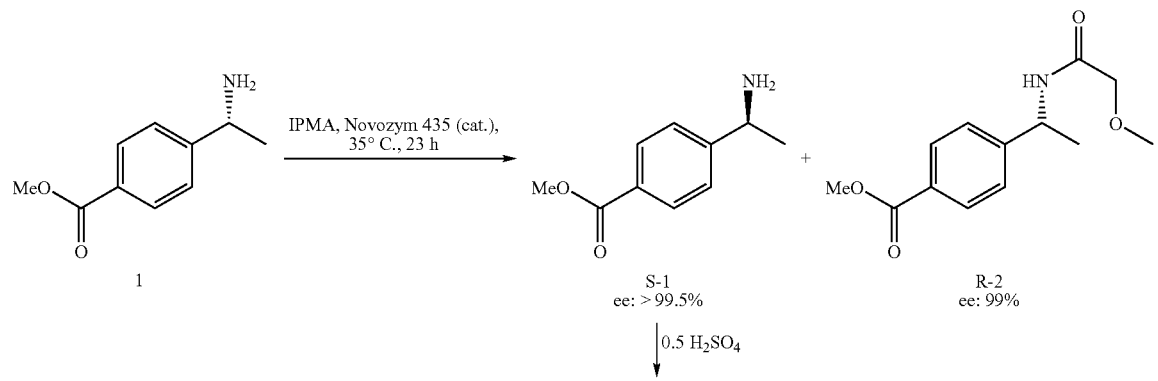

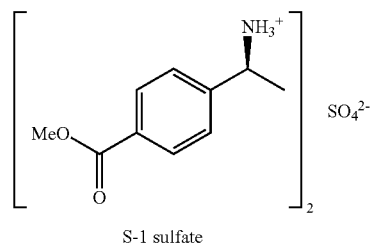

Procedure:

Isopropyl methoxyacetate IPMA (19.8 g, 0.15 mol) and Novozym 435 (500 mg) were added to a solution of methyl 4-(1-aminoethyl)benzoate 1 (17.9 g, 0.1 mol) in toluene (150 ml) and stirred at room temperature. HPLC analysis after 24 hours showed that all R-1 had been converted to the R-amide R-2, and only unreacted S-amine S-1 was now detectable. The enzyme was filtered off through kieselguhr with suction, the residue on the filter was washed with toluene (20 ml) and sulfuric acid (6.45 g of a 38% strength solution in water, 25 mmol) was added to the stirred filtrate. A voluminous white precipitate separated out. The precipitated salt was filtered off with suction, washed with toluene (2×20 ml) and the residue on the filter was recrystallized from water (10 ml). 8.9 g (78%) of sulfate S-1 were isolated as a crystalline white solid, and the S-amine S-1 bound therein was enantiopure according to HPLC analysis. Melting point: 280° C. (decomposition), optical rotation: $[\alpha]_D = -3.5°$ (c=1 in $H_2O$).

The combined toluene filtrates were washed once more with water (10 ml), dried over sodium sulfate and concentrated. The remaining residue was freed of residual solvent under oil pump vacuum at 50° C. 11 g (88%) of R-amide R-2 were recovered as oily solid (m.p.: 50-60° C.) which was 90% pure according to GC analysis.

$^1$H—NMR-Spectra:
Amine 1:
$^1$H—NMR (400 MHz, $CDCl_3$) δ=1.40 (d, J=7 Hz, 3H); 1.60 (s, broad, 2H), 3.90 (s, 3H), 4.15 (q, J=7 Hz, 1H), 7.45 and 8.03 (AA', BB' system, $J_{AB}$=10.7 Hz, 4H).

S-Amine Sulfate S-1 Sulfate:
$^1$H—NMR (400 MHz, $D_2O$) δ=1.65 (d, J=7 Hz, 3H); 3.95 (s, 3H), 4.65 (q, J=7 Hz, 1H), 7.60 and 8.10 (AA', BB' system, $J_{AB}$=10.7 Hz, 4H).
R-Amide R-2:
$^1$H—NMR (400 MHz, $CDCl_3$) δ=1.55 (d, J=7 Hz, 3H); 3.42 (s, 3H), 3.88 and 3.93 (AB system, $J_{AB}$=15 Hz, 2H), 3.90 (s, 3H), 5.23 (sept, J=7 Hz, 1 H), 6.80 (d (broad), J=7 Hz, 1H), 7.40 and 8.03 (AA', BB' system, $J_{AB}$=10.7 Hz, 4H).

We claim:
1. A method for preparing optically active methyl 4-(1-ammoniumethyl)benzoate sulfate comprising reacting racemic methyl 4-(1-aminoethyl)benzoate with an acylating agent in the presence of a lipase to give optically active methyl 4-(1-aminoethyl)benzoate and subsequently precipitating the optically active methyl 4-(1-ammoniumethyl)benzoate sulfate by adding sulfuric acid.
2. The method of claim 1, wherein said acylating agent is methoxyacetic ester.
3. The method of claim 1, wherein said lipase is Novozyme® 435.
4. The method of claim 1, wherein said reaction is carried out in a solvent.
5. The method of claim 1, wherein said lipase is removed from the reaction before the addition of said sulfuric acid.
6. Methyl (S)-4-(1-ammoniumethyl)benzoate sulfate.
7. Methyl (R)-4-(1-ammoniumethyl)benzoate sulfate.

* * * * *